United States Patent [19]
Riesgraf et al.

[11] Patent Number: 5,959,019
[45] Date of Patent: Sep. 28, 1999

[54] TOPICAL TALE CONTAINING COMPOSITIONS

[75] Inventors: Diane Riesgraf, Belle Mead; Dean T. Su, Princeton Junction, both of N.J.

[73] Assignee: Colgate-Palmolive Company, New York, N.Y.

[21] Appl. No.: 08/916,897

[22] Filed: Aug. 22, 1997

[51] Int. Cl.$^6$ .................................. A61K 7/48; C08J 3/02
[52] U.S. Cl. .................... 524/451; 424/78.02; 424/78.03
[58] Field of Search .............................. 424/78.02, 78.03; 524/451

[56] References Cited

U.S. PATENT DOCUMENTS

| | | | |
|---|---|---|---|
| 4,309,411 | 1/1982 | Toida et al. | 424/78.03 |
| 5,013,545 | 5/1991 | Blackman et al. | 424/78.02 |
| 5,143,723 | 9/1992 | Calvo et al. | 424/78.03 |
| 5,288,493 | 2/1994 | Martion et al. | 424/78.02 |
| 5,607,980 | 3/1997 | McAtee et al. | 424/78.03 |
| 5,688,831 | 11/1997 | El-Nokaly et al. | 424/78.02 |

FOREIGN PATENT DOCUMENTS 60-81120  5/1985  Japan .

OTHER PUBLICATIONS

BF Goodrich, Pemulen Polymeric Emulsifiers, Apr. 1990, 1–6.
B.F. Goodrich, Pemulen Polymeric Emulsifiers TDS 124 Revised, Jan. 2, 1991, 1–11.
Seppic, Sepigel 305, May 1990, 1–16.

*Primary Examiner*—Peter F. Kulkosky
*Attorney, Agent, or Firm*—Martin B. Barancik

[57] ABSTRACT

A composition comprising
  a) about 40 to about 85 wt. % of water,
  b) about 12 to about 50 wt. % of talc
  c) an acrylate/$C_{10}$/$C_{30}$ alkyl acrylate cross polymer, emulsifier and thickening agent in quantities effective to emulsify composition and provide increased viscosity to the aqueous composition, and
  d) a polyacrylamide in composition thickening and stabilizing quantities.

7 Claims, No Drawings

TOPICAL TALC CONTAINING COMPOSITIONS

BACKGROUND OF THE INVENTION

Talc containing compositions have been utilized on people's skins, particularly young baby's skin for many decades. It is generally applied in powder form and is spread with an applicator or the palm of one's hand to an adult or a baby's body. It is dusty and can be wasteful. For some years now, there have been attempts to place talcs into liquid compositions. These compositions are spreadable, preferably flow, and should be stable i.e. have no visible precipitate of the talc, have no discoloration over time and be capable of being evenly dispensed on a baby's skin when the liquid formulation is applied onto the skin. The stability of the system should not be temperature sensitive within reasonable ranges. There should be no separation at high temperatures in order to be a quality product fit for the skin of a child, preferably a baby's, skin.

A new composition has been designed which brings about a stable, easily applicable, composition suitable for a baby's skin. As opposed to the usual oil in water compositions, this is primarily talc and water together with specific gelling material(s) and a consistency enhancer. Additionally, emollients can be present which add to the pleasant skin feel of the applied talc composition.

SUMMARY OF THE INVENTION

In accordance with the invention there is a composition comprising a) about 40 to about 85 wt. % of water, b) about 12 to about 50 wt. % of talc, c) an acrylate/$C_{10}$–$C_{30}$ alkyl acrylate cross polymer emulsifier and thickening agent in quantities effective to emulsify the composition and provide increased viscosity to the aqueous composition, and d) a polyacrylamide in composition thickening and stabilizing quantities.

Additionally, various skin feel materials may be added so as to increase the pleasantness to the a person's skin, particularly a baby's skin. Emollients can be employed to achieve this effect without disturbing the basic stability of the liquid talc emulsified and thickened composition.

DETAILED DESCRIPTION OF THE INVENTION

A significant quantity of the composition is water. The water may vary from approximately 40 to about 85 wt. % of the composition preferably from about 50 to about 75 wt. % water. A purified water is preferably employed such as deionized or irradiated.

The other significant portion of the composition is talc. The talc may be any type of talc normally employed such as a Chinese, Italian or Australian talc. Talc is generally a silicate containing composition of relatively small particle size which can provide a slippery feeling to a person's skin. Usually it is applied as a dry powder. Because of the two emulsification gellation type components in the composition, the talc can be suspended in water in an emulsified type composition wherein the composition maintains its stability but the talc is precipitated upon the person's skin when the "liquid talc" composition is applied. The talc is present in the final composition in quantities ranging from about 12 to about 50 wt. %, preferably about 15 to about 40 wt. % of the composition, more preferably about 18 to about 30 wt. % of the composition.

The basic emulsification and thickening i.e. gellation agent employed is an acrylate/$C_{10}$–$C_{30}$ alkyl acrylate cross polymer. This is a copolymer of $C_{10}$–$C_{30}$ alkyl acrylates and one or more monomers of acrylic acid. Methylacrylic acid or one or more lower esters of these acids such as methyl, ethyl, propyl or isopropyl can be employed. The polymer is cross-linked with an allyl ether of sucrose or an allyl ether of pentaerythritol. Generally because of the acidic nature of the polymer, it is neutralized with a small amount of weak base such as an amine compound, for example triethanolamine. The polymers of this type are commercially available from Goodrich as Carbopol 1342 and Pemulen-TR1, also available from Goodrich. The quantity of this polymer which can be used in the composition to bring about emulsification, i.e. the suspension of the solid talc in water as well as thickening of the suspension is relatively small. Generally, from about 0.1 to about 0.6 wt. % of the unneutralized cross polymer can be employed. Preferably the quantity of the cross polymer is from about 0.2 to about 0.4 wt. % of the composition. The neutralizing agent is sufficient to bring about a pH of the polymer in water of about 6.5 to about 7.5 essentially a pH of about 7 of the polymer.

Also present in the composition is a polyacrylamide. This material functions as a thickening and stabilizing material for the overall composition. The quantity of the polyacrylamide is generally from about 0.3 to about 1.5 wt. % of the composition. Various polyacrylamides are commercially available such as Reten 420 from Hercules and materials which contain polyacrylamides such as Akypomine P 191 available from Chem-Y and Sepigel 305 from Seppic. The latter two compositions are sold as mixtures with other materials so as to bring about ease of handling and a quickly appearing gel when brought into contact with water. For example, the Sepigel 305 also contains small quantities of a $C_{10}$ to $C_{16}$, average $C_{12}$ to $C_{14}$ isoparaffin and a small quantity of an ethoxylated alcohol, specifically laureth-7. When using such a mixture as Sepigel 305 the amount of the total material is from about 0.1 to about 5.0 wt. % of the composition; preferably about 1 to about 3 wt. %. The amount of the isoparaffin is approximately equal to the polyacrylamide but can be up to about 25 wt. % more or less than the polyacrylamide. The ethoxylated alcohol is substantially less than the polyacrylamide, approximately 10 to 30 wt. % of the polyacrylamide. The polyacrylamide is preferably about 30 to about 40 wt. % of the Sepigel 305. The remainder of the Sepigel 305 is substantially water.

The viscosity of the final composition can vary from about 800 to more than 50,000 centipoise as measured on a Brookfield viscometer at a temperature of 25° C. At the lower viscosities a spindle #5 at 20 rpm is used. At the upper end a T-C bar at 5 rpm is used. The viscosity is preferably from about 1,000 to about 12,000 centipoise using a number 5 spindle at 20 rpm. Interestingly, the quantity of talc present in the composition can go up to as high as about 50 wt. % or more and still maintain the characteristics of spreadability, stability and the like while providing a creamy consistency to the composition. Still further, the viscosity of a 35 wt. % talc composition is very similar to that of a 25 wt. % talc composition and remains lotion like in consistency. The pH of the overall composition can vary from about 5.0 to about 7.5 but is preferably from about 6.0 to about 7.0. Such viscosity and pH will bring about a "liquid talc" composition which spreads, preferably flows and has great stability at 49° C., that is no visible precipitate of talc over a period of about 4 weeks. In this time period no visible discoloration should be present in the composition. Further, the talc is capable of even dispersion on a person's skin as opposed to a clumping of talc or areas of non-dispersion when the liquid formulation is applied to the skin. The composition should not only be stable at room temperature but at temperatures significantly above room temperature. For example, stability, i.e. no visible precipitation or discoloration should be observed at temperatures of 49° C. over a period of about 4 weeks.

As stated previously in order to enhance skin feel, various emollients can be added to the composition. Examples of such emollients are essentially almost infinite. However, such emollient families include the following: silicone oils and gums and modifications thereof such as linear cyclopolydimethylsiloxocanes; amino, alkyl, alkylaryl and aryl silicone oils; fats and oils including natural fats and oils such as jojoba, soybean, rice bran and the like; waxes such as lanolin and beeswax; hydrocarbons such as liquid parrafins, petrolatums, mineral oil and the like; free-fatty acids such as lauric myristic, palmitic, and stearic; higher alcohols ethoxylated or not such as lauryl, myristyl, stearyl, behenyl, and the like; esters such as long-chain esters of long-chain acids, long-chain esters of short-chain acids, and short-chain esters of long-chain acids. Examples of the last materials include acetyl octanoate, butyl stearate, glycerol monostearate other esters such as long-chain esters of phosphoric acid, ethoxylated or non-ethoxylated, and the like. When these emollients are present in their emollient skin feel enhancing quantities, for example 0.1 to about 5.0 wt. %, preferably about 0.2 to about 1.5% the basic characteristics of the composition previously commented upon should not be fundamentally changed. However, it should be noted that some of these emollients because of their hydrophobic nature may actually assist as emulsifiers for the system.

The compositions of the invention may be readily prepared by processes known in the art. For example, the water, cross polymer, polymeric neutralizer, talc, and any pH adjuster such as a small quantity of citric acid can be brought together and mixed in a vessel. In a separate vessel the polyacrylamide and any emollients, such as those mentioned above, can be mixed. These two vessel contents can then be combined with further mixing. To this admixture can be added various standard additional agents, such as, for example, a fragrance and a preservative system.

Below are examples of the invention. These examples are meant to be illustrative of the invention and not unduly limit the basic inventive concept.

EXAMPLES

Example 1

| Component | Quantity wt. % |
|---|---|
| Deionized Water | 75.780 |
| Pemulen TR-1 | 0.300 |
| Triethanolamine | 0.200 |
| Talc | 20.000 |
| Isostearath-2 Phosphate | 1.000 |
| Octyl Palmitate | 0.350 |
| Sepigel 305 | 2.000 |
| Fragrance | 0.300 |
| Preservative | 0.070 |

The octylpalmitate is an emollient. The isostearath-2 phosphate provides additional skin feel.

This composition brings about a liquid talc which is flowable, stable at a temperature of 49° C. for a period of 4 weeks and shows no visible discoloration or precipitation in that time period. The pH of the formulation is 5.1 at 25° C. and has a viscosity of 28,600 centipoise using a Brookfield RVT viscometer at 25° C. with spindle # 6 and 10 rpm. When applied to a person's skin the talc is evenly dispersed and provides excellent feel to the skin.

Example 2

The same formulations as in Example 1 is employed except 0.25 ml of triethanolamine is utilized to neutralize the polyacrylate polymer. The water is reduced by the increased amount of triethanolamine. Essentially the same results as in Example 1 are achieved. The pH of the formulation is 6.2.

Example 3

The same formulation as in Example 2 is employed except that Sepigel 305 is decreased 0.5 wt. % to 1.5 wt. % of the composition and the quantity of water is increased. Essentially the same results as in Example 2 are achieved.

Example 4

The same formulation as in Example 2 is employed except that the Sepigel 305 is reduced to 1.0 wt. % and the water is increased. Essentially the same results as in Example 2 are achieved.

Example 5

The same formulation as in Example 1 is employed except that Pemulen TR-1 is reduced to 0.2 wt. % and the Sepigel 305 is decreased to 1.0 wt. % and the water is increased. Essentially the same results as in Example 1 are obtained.

Example 6

The same formulation as in Example 5 is employed except that Pemulen TR-I is reduced to 0.15 wt. %. The pH of the composition is 6.4 and the viscosity is 11220 centipoise. Using a RVT spindle #5 at 20 rpm. After being held at 49° C. for 4 weeks there is no visible separation or discoloration.

Example 7

The same formulation as in Example 6 is employed except that the talc is increased to 35 wt. % and the water reduced appropriately. The formulation is spreadable, has a pH of 6.3 and viscosity of 12,280 centipoise at 25° C, using a RVT spindle #5 at 20 rpm. After being held at 49° C. for 4 weeks there is no visible separation or discoloration.

Example 8

The same formulation as in Example 7 is employed except that the talc is increased to 50 wt. % and the water is reduced appropriately. The formulation is spreadable, has a pH of 6.3 and a viscosity of 30,700 centipoise at 28° C. using a RVT spindle #6 at 10 rpm. After being held at 49° C. for 4 weeks, there is no visible separation or discoloration.

What is claimed is:

1. A thickened, spreadable aqueous suspension comprising
   a. about 40 to about 85 wt. % water,
   b. about 12 to about 50 wt. % talc,
   c. a copolymer of C10–C30 ethyl acrylates and one or more monomers of acrylic acid, methacrylic or one or more lower esters of these acids selected from the group consisting of methyl, ethyl, propyl or isopropyl cross linked with an allyl ether of sucrose or an allyl ether of pentaerythritol in quantities effective to spread the talc and provide increased viscosity to the composition, and
   d. a polyacrylamide in composition thickening and stabilizing quantities wherein there is no visible precipitate of talc over a period of about 4 weeks at 49° C.

2. The claim in accordance with claim 1 wherein the talc is from about 15 to about 35 wt. % of the composition.

3. The claim in accordance with claim 1 wherein the cross polymer is from about 0.1 to about 0.6 wt. % of the composition.

4. The claim in accordance with claim 1 wherein the polyacrylamide is from about 0.3 to about 1.0 wt. % of the composition.

5. The claim in accordance with claim 1 wherein the cross polymer is essentially neutralized.

6. The claim in accordance with claim 4 wherein also present in the composition is an isoparaffin having from about 10 to about 14 carbon atoms inclusive, and an ethoxylated primary alcohol having from about 10 to about 18 carbon atoms, inclusive.

7. The composition in accordance with claim 1 prepared by mixing
   a) about 40 to about 85 wt. % of water,
   b) about 12 to about 50 wt. % of talc,
   c) an acrylate/$C_{10}$/$C_{30}$ alkyl acrylate cross polymer, suspending and thickening agent in quantities effective to suspend the talc and provide increased viscosity to the aqueous composition, and
   d) a polyacrylamide in composition thickening and stabilizing quantities.

* * * * *